United States Patent
Lichtenstein

(10) Patent No.: US 8,583,215 B2
(45) Date of Patent: Nov. 12, 2013

(54) REDUCTION OF CATHETER ELECTRODE LOADING

(75) Inventor: Yoav Lichtenstein, Raanana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 284 days.

(21) Appl. No.: 12/613,109

(22) Filed: Nov. 5, 2009

(65) Prior Publication Data

US 2011/0137151 A1    Jun. 9, 2011

(51) Int. Cl.
*A61B 5/05* (2006.01)

(52) U.S. Cl.
USPC .......................................... 600/424; 600/372

(58) Field of Classification Search
USPC .............................. 600/372–382, 424; 333/12
See application file for complete search history.

(56) References Cited

U.S. PATENT DOCUMENTS

| | | | |
|---|---|---|---|
| 5,983,126 A | 11/1999 | Wittkampf | |
| 6,052,038 A * | 4/2000 | Savicki | ............................ 333/12 |
| 2006/0173251 A1 | 8/2006 | Govari et al. | |
| 2007/0038078 A1 | 2/2007 | Osadchy | |
| 2007/0055125 A1 | 3/2007 | Anderson et al. | |
| 2008/0161681 A1 | 7/2008 | Hauck | |
| 2010/0057070 A1 | 3/2010 | Behnke et al. | |

FOREIGN PATENT DOCUMENTS

WO    WO 99/39650    8/2009

OTHER PUBLICATIONS

EP Search Report No. EP 10 25 1900 Dated Feb. 10, 2011.

* cited by examiner

*Primary Examiner* — Parikha Mehta
(74) *Attorney, Agent, or Firm* — Louis J. Capezzuto

(57) ABSTRACT

A method for position sensing includes inserting a probe having a first probe-electrode and a second probe-electrode into a body of a subject, and coupling body-surface electrodes to a surface of the body. Currents passing between the first probe-electrode and the body-surface electrodes are measured, using first circuitry coupled to at least the first probe-electrode and having a first electrical ground, and position coordinates of the probe are determined responsively to the measured currents. Second circuitry, having a second electrical ground, is coupled to at least the second probe-electrode, and the first electrical ground is isolated from the second electrical ground.

14 Claims, 6 Drawing Sheets

REDUCTION OF CATHETER ELECTRODE LOADING

FIELD OF THE INVENTION

The present invention relates generally to sensing the position of an object placed within a living body, and specifically to position sensing using impedance measurements.

BACKGROUND OF THE INVENTION

A wide range of medical procedures involves placing objects, such as sensors, tubes, catheters, dispensing devices, and implants, within the body. Real-time imaging methods are often used to assist medical practitioners in visualizing the object and its surroundings during these procedures. However, in many situations, real-time imaging is not possible or desirable. Instead, systems for obtaining real-time spatial coordinates of the internal object are often utilized. Many such position-sensing systems have been developed or envisioned in the prior art.

For example, U.S. Pat. No. 5,983,126, to Wittkampf, whose disclosure is incorporated herein by reference, describes a system in which catheter position is detected using electrical impedance methods. U.S. Patent Application Publications 2006/0173251, to Govari et al., and 2007/0038078, to Osadchy, whose disclosures are incorporated herein by reference, describe impedance-based methods for sensing the position of a probe by passing electrical currents through the body between an electrode on the probe and a plurality of locations on a surface of the body.

SUMMARY OF THE INVENTION

Embodiments of the present invention provide efficient means and methods for determining in real-time the position of a probe placed within a living body, based on measurement of currents passing between electrodes on the probe and body surface electrodes. The methods and means described hereinbelow are used to reduce distortion of the measured currents, thus enhancing the accuracy of the position measurements.

There is therefore provided, in accordance with an embodiment of the present invention, a method for position sensing, including:

inserting a probe including a first probe-electrode and a second probe-electrode into a body of a subject;

coupling body-surface electrodes to a surface of the body;

measuring, using first circuitry coupled to at least the first probe-electrode and having a first electrical ground, currents passing between the first probe-electrode and the body-surface electrodes;

determining position coordinates of the probe responsively to the measured currents;

coupling second circuitry, having a second electrical ground, to at least the second probe-electrode; and isolating the first electrical ground from the second electrical ground.

In some embodiments, isolating the first electrical ground further includes coupling the first electrical ground to the second electrical ground via a predetermined inter-ground coupling impedance.

Typically, the value of the inter-ground coupling impedance is selected to maximize an accuracy of determining the position coordinates.

In some embodiments, the inter-ground coupling impedance is between 500 and 5000 Ohm.

Typically, inserting the probe includes passing the probe into a heart of the subject, and coupling the second circuitry includes measuring an electrical activity of the heart using at least the second probe-electrode.

In some embodiments, both of the first and second probe-electrodes are coupled for use in both determining the position coordinates and measuring the electrical activity.

In further embodiments, the first circuitry includes a front-end including an isolation transformer having a primary winding and a secondary winding, which is coupled to at least the first probe-electrode. In such embodiments, isolating the first electrical ground from the second electrical ground may include coupling the secondary winding of the isolation transformer to the first electrical ground while the primary winding is coupled to the second electrical ground.

In some embodiments, measuring the currents includes coupling a front end having an output impedance typically greater than 100,000 Ohm to transmit the currents through at least the first probe-electrode.

There is also provided, in accordance with an embodiment of the present invention, a medical system, including:

a probe adapted to be inserted into a body of a subject, the probe including a first probe-electrode and a second probe-electrode;

a plurality of body-surface electrodes, which are adapted to be fixed to a surface of the body at respective locations;

first circuitry, coupled to at least the first probe-electrode and configured to measure currents passing between the first probe-electrode and the body-surface electrodes, the first circuitry having a first electrical ground;

a positioning processor configured to determine position coordinates of the probe responsively to the measured currents; and second circuitry, coupled to at least the second probe-electrode and having a second electrical ground, which is isolated from the first electric ground.

The present invention will be more fully understood from the following detailed description of the embodiments thereof, taken together with the drawings in which:

DETAILED DESCRIPTION OF THE EMBODIMENTS

Figure 1:
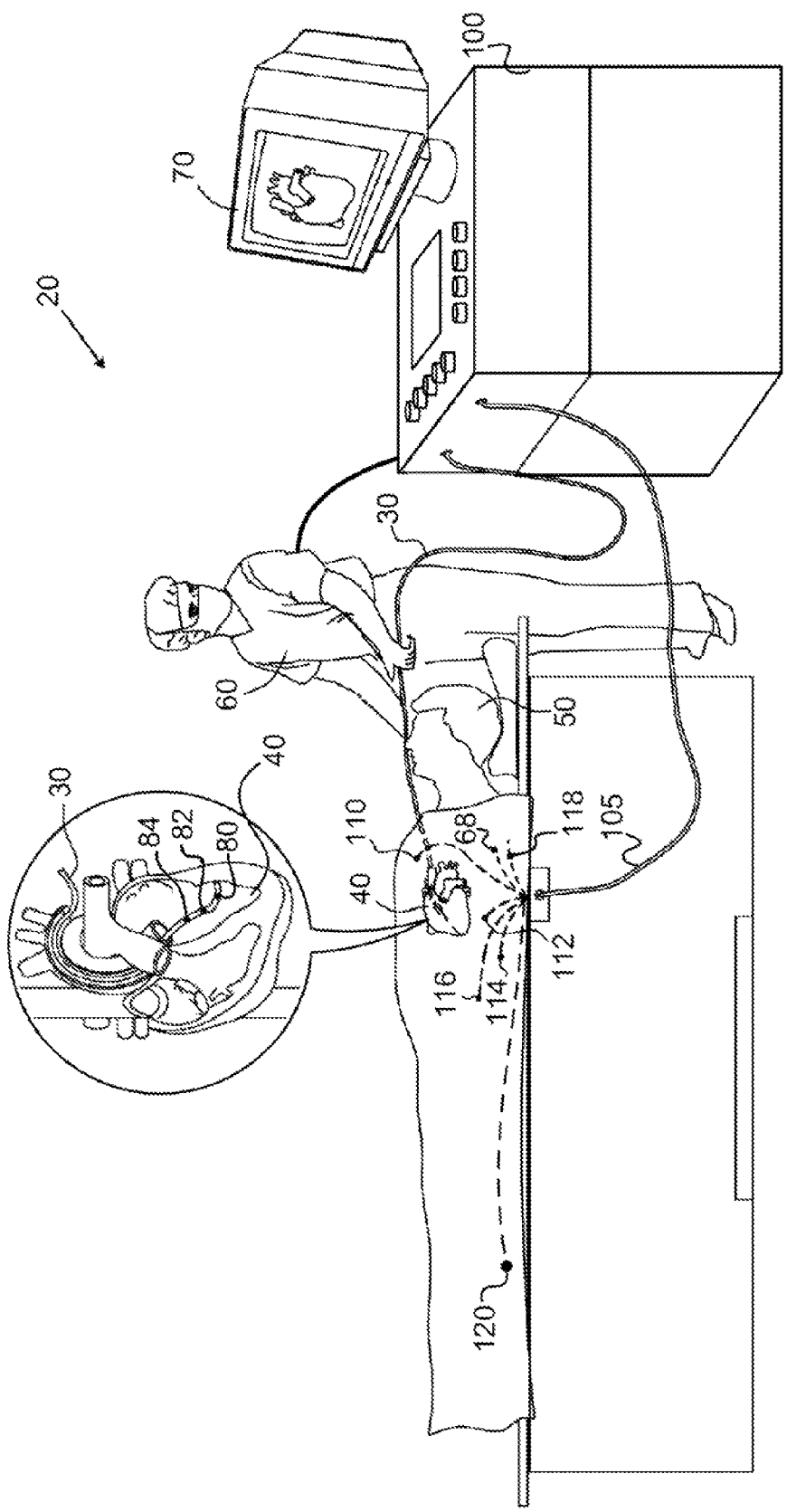
FIG. 1 is a schematic pictorial illustration of a medical system, in accordance with an embodiment of the present invention.

FIG. 1 is a schematic pictorial illustration of a medical system 20, in accordance with an embodiment of the present invention. System 20 comprises a probe 30, such as a catheter, which is adapted to be inserted into an internal body cavity, such as a chamber of a heart 40, of a subject 50. Typically, the probe is used by a practitioner 60 for one or more medical diagnostic or therapeutic functions, such as intra-cardiac electrocardiography (ECG), mapping electrical potentials in the heart, performing ablation of heart tissue, or other medical functions. In order to facilitate effective application of the medical procedure, system 20 is adapted to determine the position of probe 30 within the body of the subject. The position of the probe, along with other diagnostic and/or therapeutic data, is typically displayed to practitioner 60 on monitor 70, or presented by means of other suitable media.

The distal tip of probe 30 comprises a plurality of electrodes 80, 82 and 84, referred to herein as probe-electrodes. The probe-electrodes are connected by wires through the insertion tube of probe 30 to a control unit 100, which comprises first circuitry adapted to determine the position of the probe within the subject's body and second circuitry adapted to perform one or more diagnostic or therapeutic functions. The first and second circuitries are referred to herein as the positioning and functional circuitries, respectively, and are shown in detail in the figures that follow. The term functional refers herein to one or more medical diagnostic or therapeutic functions of system 20 (e.g., measurement and mapping of cardiac electrical signals). One or more of the probe-electrodes (referred to herein as the positioning probe-electrodes) are coupled to the positioning circuitry, while one or more of the probe-electrodes (referred to herein as the functional probe-electrodes) are coupled to the functional circuitry. Typically, the same probe-electrodes are utilized both for positioning and for medical diagnostic or therapeutic functions. Therefore, the first and second sets of electrodes typically overlap. However, in some cases, the two sets of electrodes may be disjoint.

Control unit 100 is further connected by wires through one or more cables 105 to a plurality of body-surface electrodes 110, 112, 114, 116, 118, and 120, which are coupled to a body-surface (i.e., the skin) of the subject. The body-surface electrodes typically comprise adhesive skin patches. In alternative embodiments of the invention, the body-surface electrodes may vary in number and may take other forms. The body-surface electrodes comprise a set of first body-surface electrodes 110, 112, and 114, referred herein as positioning body-surface electrodes, which are coupled to the positioning circuitry. The body-surface electrodes may additionally comprise one or more second body-surface electrodes 116, 118, and 120, referred herein as functional body-surface electrodes, which are connected to the functional circuitry. Typically, the two sets of body-surface electrodes are disjoint, but in some cases, the two sets may overlap.

The positioning circuitry of the control unit is adapted to drive and measure electric currents, referred herein as positioning-currents, between the positioning probe-electrodes and the positioning body-surface electrodes. Responsive to the measured positioning currents, a positioning processor (shown in FIG. 2), which is typically incorporated within control unit 100, estimates the coordinates the distal end of probe 30 within the body. The positioning processor typically comprises a general-purpose computer processor, which is programmed in software to estimate the probe coordinates according to methods described in the above-cited Patent Application Publications 2006/0173251 and 2007/0038078. Additionally or alternatively, the positioning processor may employ other suitable positioning methods.

Probe coordinate estimation is typically based on correspondence between positioning currents and respective distances of intra-body paths. For example, we may denote the distances from probe electrode 80 to body-surface electrodes 110, 112, and 114 by D1, D2, and D3, respectively, and denote the positioning currents from probe electrode 80 to body-surface electrodes 110, 112, and 114 by I1, I2, and I3, respectively. According to methods described in the above-cited patent applications, the ratio of distances D1:D2:D3 can be estimated based on the ratio of currents I1:I2:I3. The coordinates of probe electrode 80 can than be derived from the estimated ratio D1:D2:D3.

Since probe coordinates calculation rely on positioning currents between related electrodes, it is desirable that the positioning currents not be influenced by electrical coupling with non-related electrodes. For example, if the ratio I1:I2:I3 varies due to electrical coupling with functional probe-electrode 82, the ratio D1:D2:D3 might be incorrectly estimated. Methods according to embodiments of the present invention, which are described hereinbelow, facilitate eliminating or reducing the effect of the functional electrodes on the positioning currents, thus enabling accurate and reliable positioning of probe 30 within the subject's body.

Figure 2:
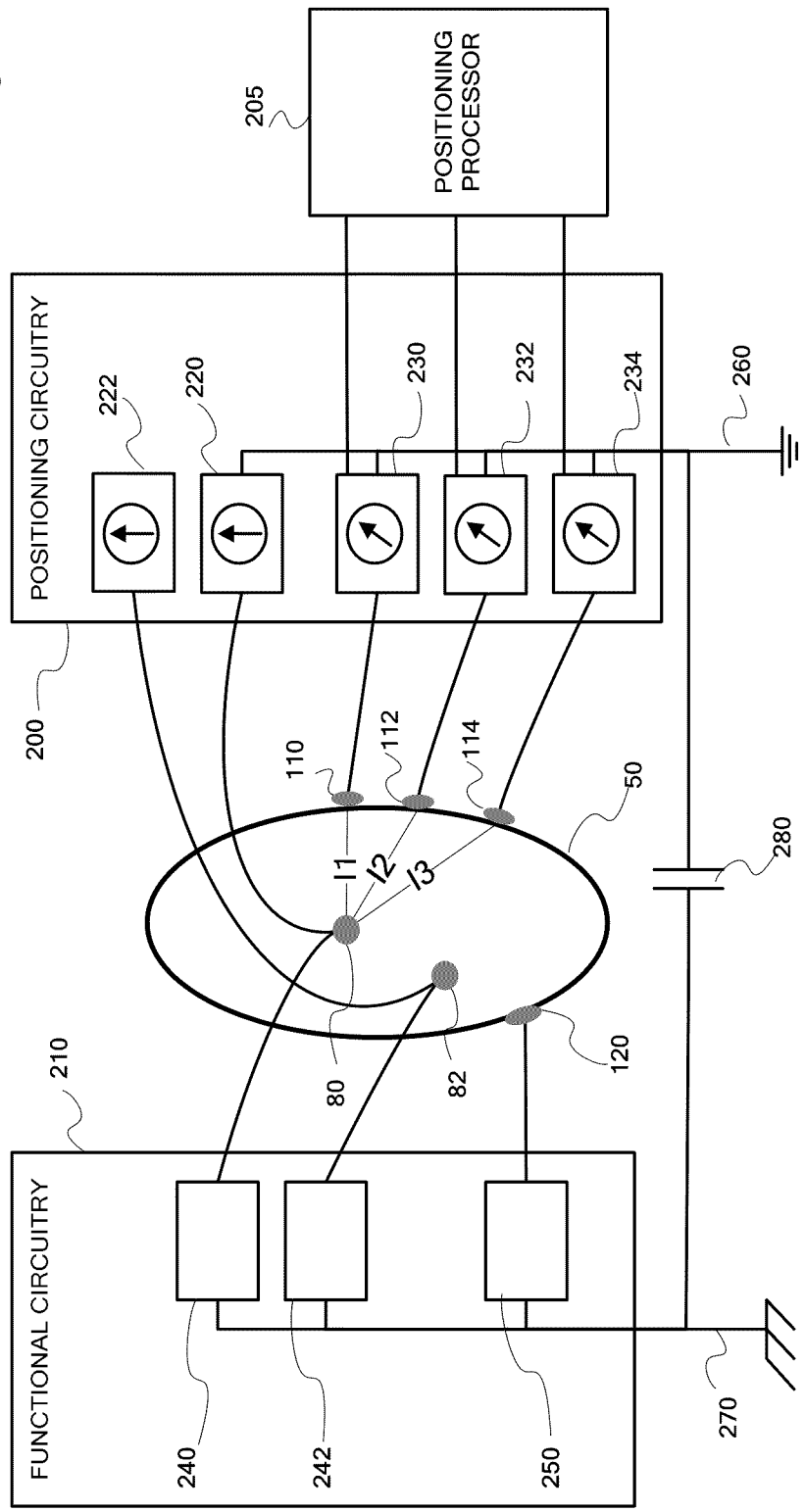
FIG. 2 is a schematic diagram, showing interaction between electrodes and associated circuitries thereof, in accordance with an embodiment of the present invention.

FIG. 2 is a schematic diagram, showing interaction between probe-electrodes and body-surface electrodes, and associated circuitries thereof, in accordance with an embodiment of the present invention. As noted above, control unit 100 (not shown explicitly in FIG. 2) comprises positioning circuitry 200, a positioning processor 205, and functional circuitry 210. Positioning circuitry 200 comprises one or more positioning probe front-ends (e.g., front-ends 220 and 222), and each positioning probe front-end is coupled to a positioning probe-electrode (e.g., probe-electrodes 80 and 82). Positioning probe front-end typically comprises a high impedance driver (such as is shown below in FIG. 6), which drives positioning currents between respective positioning probe electrode and a plurality of positioning body-surface electrodes. For example, positioning probe front-end 220 drives positioning currents I1, I2 and I3 between probe electrode 80 and body-surface electrodes 110, 112, and 114, respectively.

The impedance of positioning probe front-end 220 is typically much higher than the impedance of a path through a human body, and therefore positioning probe front-end 220 is approximately a current source. For example, a typical impedance of a path through a human body is 100 Ohm, and the output impedance of a positioning probe front-end is typically higher than 100,000 Ohm. The positioning currents are typically AC currents, for example AC currents in the range of 100-110 kHz. Therefore, the term impedance refers herein to impedance measured over the frequency range of the positioning currents, for example impedance measured over the range of 100-110 kHz.

Positioning circuitry 200 also comprises current-sensing devices 230, 232 and 234, which are coupled to positioning body-surface electrodes 110, 112 and 114, and measure the respective positioning currents I1, I2, and I3. In alternative embodiments of the invention, the positioning currents may be measured by a single current-sensing device, by means of time multiplexing.

Based on the positioning currents I1, I2, and I3, positioning processor 205 calculates the coordinates of positioning probe-electrode 80 within body 50, according to methods described in the above-cited patent applications, or according to other suitable current-based positioning methods.

Functional circuitry 210 of the control unit comprises one or more functional probe front-ends 240 and 242, which are coupled to functional probe-electrodes 80 and 82, respectively. Functional circuitry 210 may also comprise one or more functional body-surface front-ends (e.g., a body-surface front-end 250), which are coupled to functional body-surface electrodes (e.g., functional body-surface electrode 120). In cases in which functional circuitry 210 comprises ECG circuitry, the body-surface electrode attached to the right leg of the subject serves typically as a common reference for differential ECG measurements. In those cases, the right leg electrode is typically coupled to the ground of the ECG circuitry via impedance on the order of 10,000 Ohm.

Usually, grounds of distinct circuits of an electrical system are highly coupled, since all circuits of the same system are typically fed, directly or indirectly, by the same power source (e.g., the mains). Furthermore, it is a common practice to connect the grounds of all circuits of an electric system to one common ground. For example, all circuits that are implemented on the same printed circuit board (PCB) are typically connected to the same one or more ground layers of the PCB, all ground layers of all PCBs are typically connected to the system chassis, and the system chassis is typically connected to the mains ground.

However, in embodiments of the present invention, positioning circuitry 200 and functional circuitry 210 are connected to distinct grounds 260 and 270, respectively, and ground 260 is deliberately isolated from ground 270. Typically, ground 270 is implemented as one or more ground layers of one or more PCBs, which are connected to a system common ground, for example to the system chassis; while ground 260 is implemented as a dedicated return path, which is isolated from the respective PCBs ground layers, and from the system common ground. Isolating of ground 260, according to embodiments of the present invention, is employed in order to maintain the validity and accuracy of the positioning process, as elaborated hereinbelow.

In some embodiments of the present invention, isolated grounds 260 and 270 are further coupled by an inter-ground coupling impedance 280 (e.g. a capacitor), in order to eliminate or reduce the effect of parasitic couplings on the validity and accuracy of the positioning process, as elaborated further below.

Figure 3:
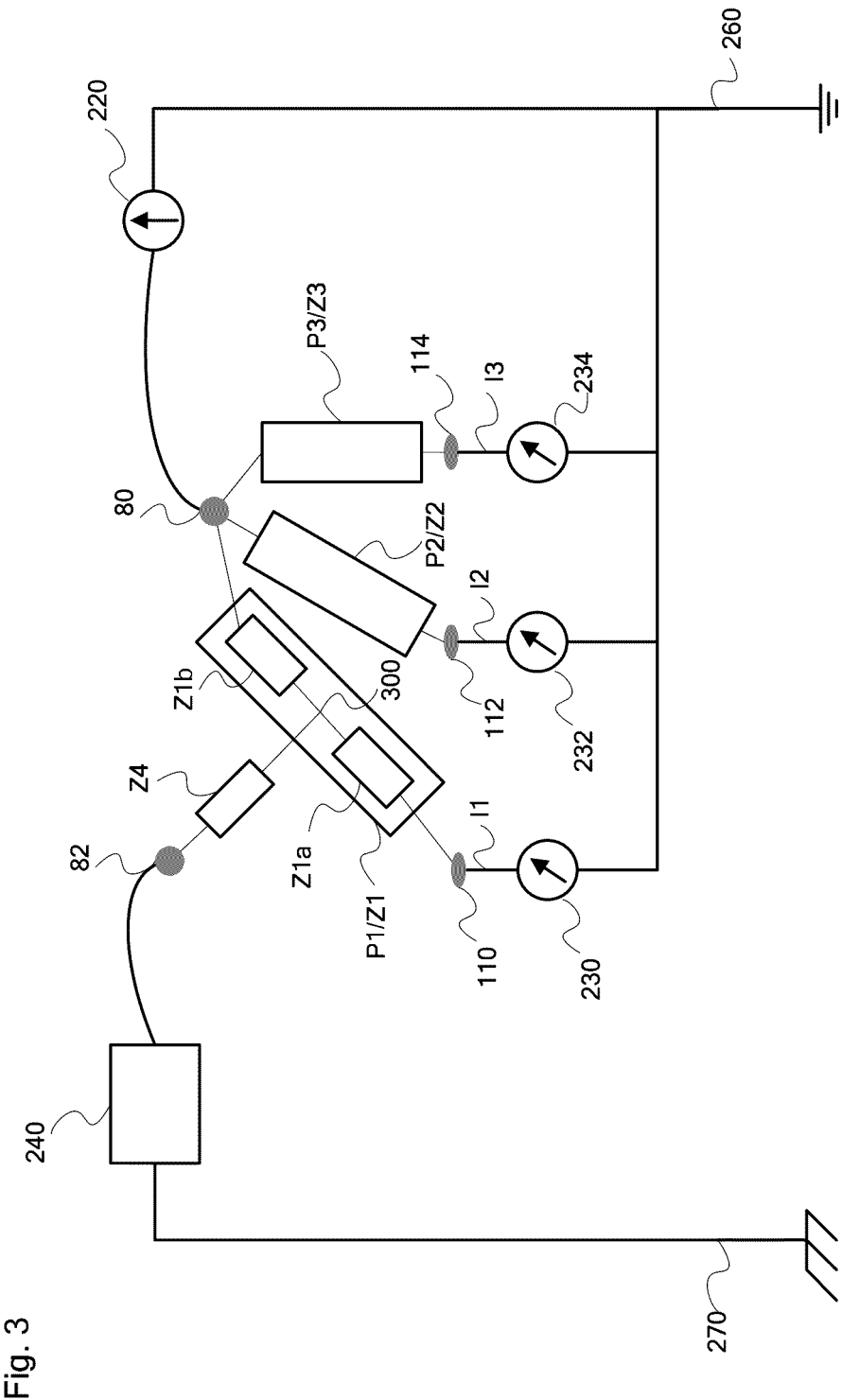
FIGS. 3, 4, and 5 are schematic electrical diagrams, illustrating influence of functional electrodes on positioning currents, in accordance with embodiments of the present invention.
Figure 4:
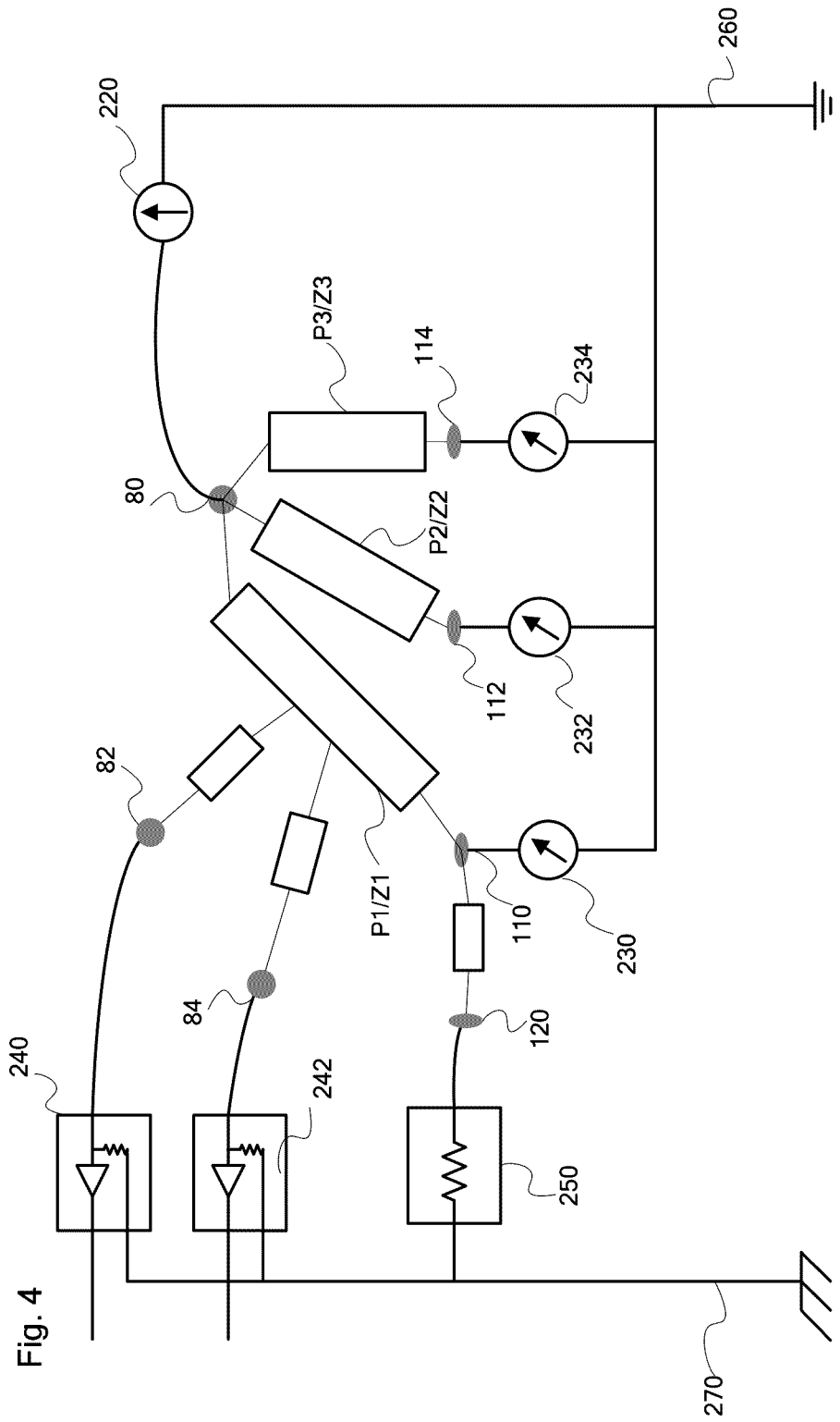
Figure 5:
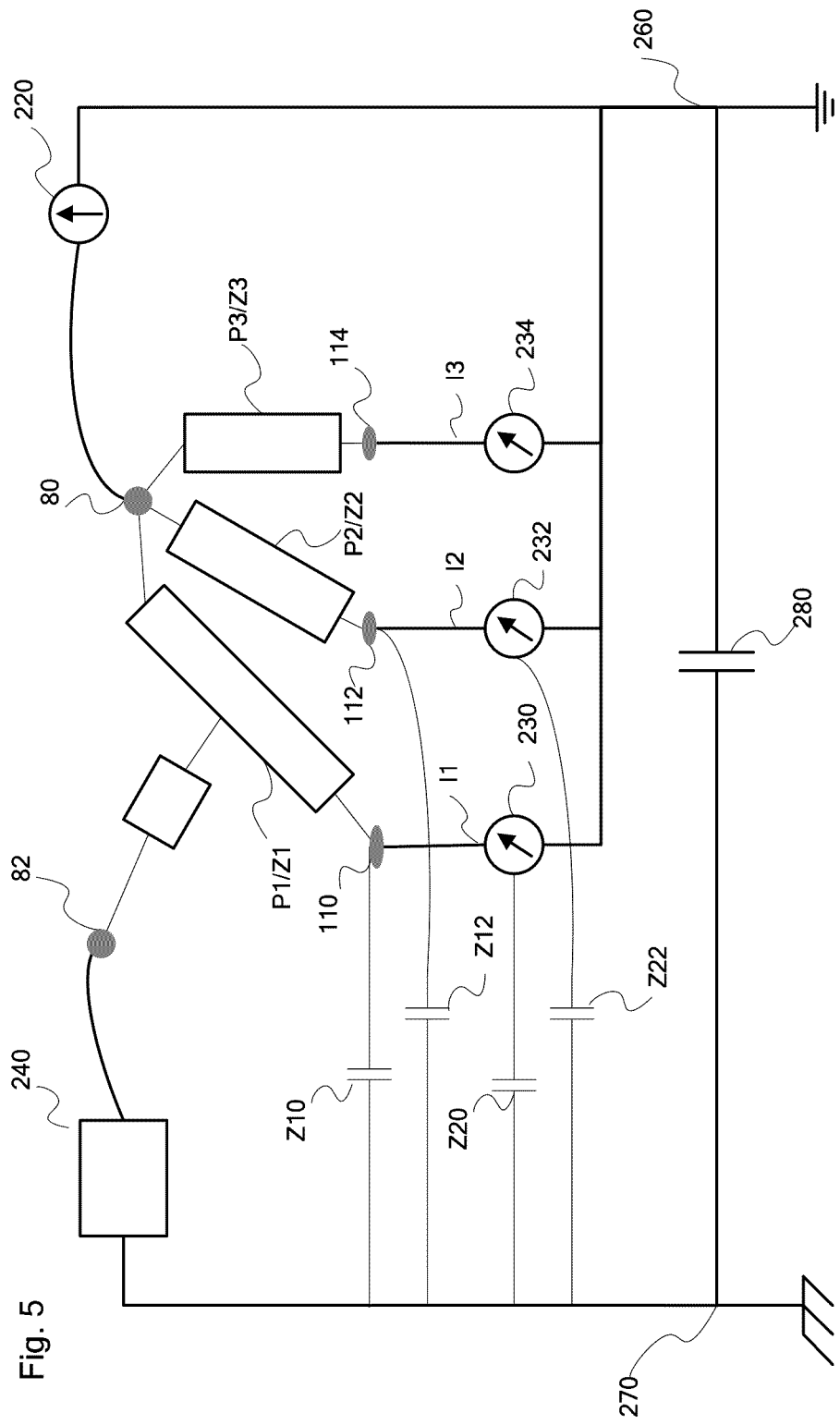

FIGS. 3, 4, and 5 are schematic electric diagrams, illustrating the potential influence of functional electrodes on positioning currents, in accordance with embodiments of the present invention. FIG. 3 illustrates the effect of functional probe-electrode 82 on positioning currents I1, I2, and I3, which flow between positioning probe-electrode 80 and body-surface electrodes 110, 112, and 114, respectively (on the assumption that there is coupling between grounds 260 and 270). Positioning currents I1, I2, and I3 are driven by front-end 220, and are measured by measurement devices 230, 232, and 234, respectively. We denote the intra-body distances between probe-electrode 80 and body-surface electrodes 110, 112, and 114, by D1, D2, and D3, respectively, as noted above. (D1, D2, and D3 are not shown in the figure). The respective intra-body paths between the probe-electrode and body-surface electrode are denoted by P1, P2, and P3, and the respective intra-body impedances by Z1, Z2, and Z3. Positioning currents I1, I2, and I3 are essentially proportional to respective impedances Z1, Z2, and Z3, which are dependent on respective distances D1, D2, and D3, and this dependency provides the basis for the operation of the positioning processor.

Since functional probe-electrode 82 is also located within the body of the subject, there are inevitable electric coupling paths between electrode 82 and paths P1, P2, and P3. FIG. 3 shows a coupling path Z4 between functional probe electrode 82 and an intermediate point 300 on path P1. Similarly, there are coupling paths between probe electrode 82 and intermediate points on paths P2 and P3. Intermediate point 300 is illustrated in FIG. 3 as breaking Z1 into two impedances $Z1a$ and $Z1b$, wherein $Z1a+Z1b=Z1$. This illustration is a simplified model of a typically much more complicated model, but it is helpful in illustrating the effect of the coupling between the functional probe electrodes and the positioning currents.

If ground 260 of the positioning circuitry were coupled to ground 270 of the functional circuitry as in systems known in the art, there would be undesired currents that flow between positioning probe-electrode 80 and ground 260, via functional probe-electrode 82. The undesired currents change the desired positioning currents, and degrade the accuracy of the positioning process. For example, if front-end 220 comprises a current source, the undesired currents reduce the desired positioning currents, but each current is typically reduced by a different amount due to geometrical and physiological factors. Consequently, the ratio of currents I1:I2:I3 changes, thus reducing the accuracy of the position measurement.

However, according to an embodiment of the present invention, ground 260 is isolated from ground 270, and therefore undesired currents cannot flow via functional probe-electrode 82. As a result, the positioning currents are not changed, and the validity and accuracy of the positioning process are maintained, regardless of the functional probe-electrodes.

FIG. 4 illustrates an embodiment in which the functional circuitry comprises ECG circuitry, and front-end 250 is coupled to electrode 120, which is placed on the subject's right leg. Since right-leg ECG electrode 120 and positioning electrodes 110, 112, and 114 are all coupled to the skin, there is inevitable electrical coupling between electrode 120 and electrodes 110, 112, and 114. (For the sake of simplicity, only the coupling with electrode 110 is shown in the figure.) Consequently, there is a parasitic electrical coupling between path P1 and ground 260, via functional probe-electrodes 82 and 84, functional probe front-ends 240 and 242, right-leg front-end 250, and right-leg electrode 120. (Similar coupling mechanisms, not shown in the figure, apply also to other paths, e.g., paths P2 and P3).

However, since the impedance of right-leg front-end 250 is typically about 10,000 Ohm, the impedance of the parasitic coupling through right-leg electrode 120 is always above 10,000 Ohm, regardless of the numbers of functional probe electrodes. Consider, for example, the case of forty functional probe-electrodes, and assume that the impedance of each functional probe front-end is about 10,000 Ohm. The collective impedance of the forty functional probe electrodes and their associated front-ends is 10,000/40=250 Ohm. This low collective impedance could interfere significantly with the positioning process. However, since the impedance of right-leg front-end 250 is 10,000 Ohm, and grounds 260 and 270 are isolated from one another, the overall parasitic impedance is as high as 10,250 Ohm, and has minor effect on the positioning process.

FIG. 5 presents an embodiment of the present invention in which grounds 260 and 270, which are deliberately isolated from each other, are further coupled by predetermined inter-ground coupling impedance 280, typically implemented by a capacitor. The goal of the inter-ground coupling impedance is to reduce the influence of possible parasitic coupling, as explained hereinbelow.

In typical configurations of system 20, there might be parasitic couplings between ground 270 and positioning body-surface electrodes 110, 112 and 114. Two such couplings, denoted by Z10 and Z12, are shown in the figure. Additionally, there might be parasitic couplings between ground 270 and measurement devices 230, 232, and 234. Two such coupling, denoted by Z20 and Z22, are shown in the figure. Parasitic couplings such as Z20 and Z22 might be caused, for example, by parasitic capacitance between the positioning circuitry (e.g., measurement devices 230 and 232) and the one or more ground layers of the PCBs. The parasitic couplings modify the readings of the measurement devices, and therefore degrade the accuracy of the positioning process. For example, parasitic couplings Z10 and Z20 (Z12 and Z22) enable flow of parasitic current from positioning probe-electrode 80, via functional probe-electrode 82, to measurement device 230 (232), respectively, and thus increase the reading of the measurement device and degrade the accuracy of the ratio I1:I2:I3.

In the embodiment shown in FIG. 5, the undesired effect of parasitic couplings, such as Z10, Z11, Z20, and Z21, is reduced by introducing inter-ground coupling impedance 280 between grounds 260 and 270. The coupling impedance 280 is typically selected to be considerably lower than the values of the parasitic impedances Z10, Z11, Z20, and Z21. Consequently, most of the parasitic currents flow through inter-ground coupling impedance 280, and the parasitic currents trough the measurements devices are reduced accordingly.

On the other hand, inter-ground coupling impedance 280 should be selected to be considerably higher than intra-body impedances Z1, Z2, and Z3, in order to maintain the benefit of the isolation between grounds 260 and 270, as elaborated above.

In a typical system, the best value of the inter-ground coupling impedance to yield maximal accuracy of the positioning process, may be determined empirically. Determining the value is facilitated by the fact that the overall accuracy of the positioning process is typically a concave function of the coupling impedance. For example, in a typical system, the total parasitic coupling is about 5,000 Ohm, and the typical intra-body impedances are about 100 Ohm. For such system, the value for the inter-ground coupling impedance should typically be about 1,000 Ohm.

FIGS. 3, 4, and 5 address the potential influence of functional probe-electrodes (e.g., probe-electrode 82) on positioning currents flowing through a positioning probe-electrode (e.g., probe-electrode 80). In principle, there might also be similar undesired influence of a first positioning probe-electrode on the positioning currents flowing from a second positioning probe-electrode.

Returning to FIG. 2, functional probe-electrode 82 is also a positioning probe-electrode, and is also coupled to positioning probe front-end 222. Therefore, undesired parasitic currents might in principle flow from positioning probe-electrode 80, via positioning probe-electrode 82 and positioning front-end 222, to ground 260. However, since the impedance of positioning-probe front-end 222 is typically much higher than intra-body impedances Z1, Z2, and Z3 (shown in FIG. 3), the effect of coupling between positioning probe-electrodes is minor. For example, the impedance of positioning probe front-end 222 is typically above 100,000 Ohm, while the values of intra-body impedances Z1, Z2, and Z3 are typically about 100 Ohm.

Figure 6:
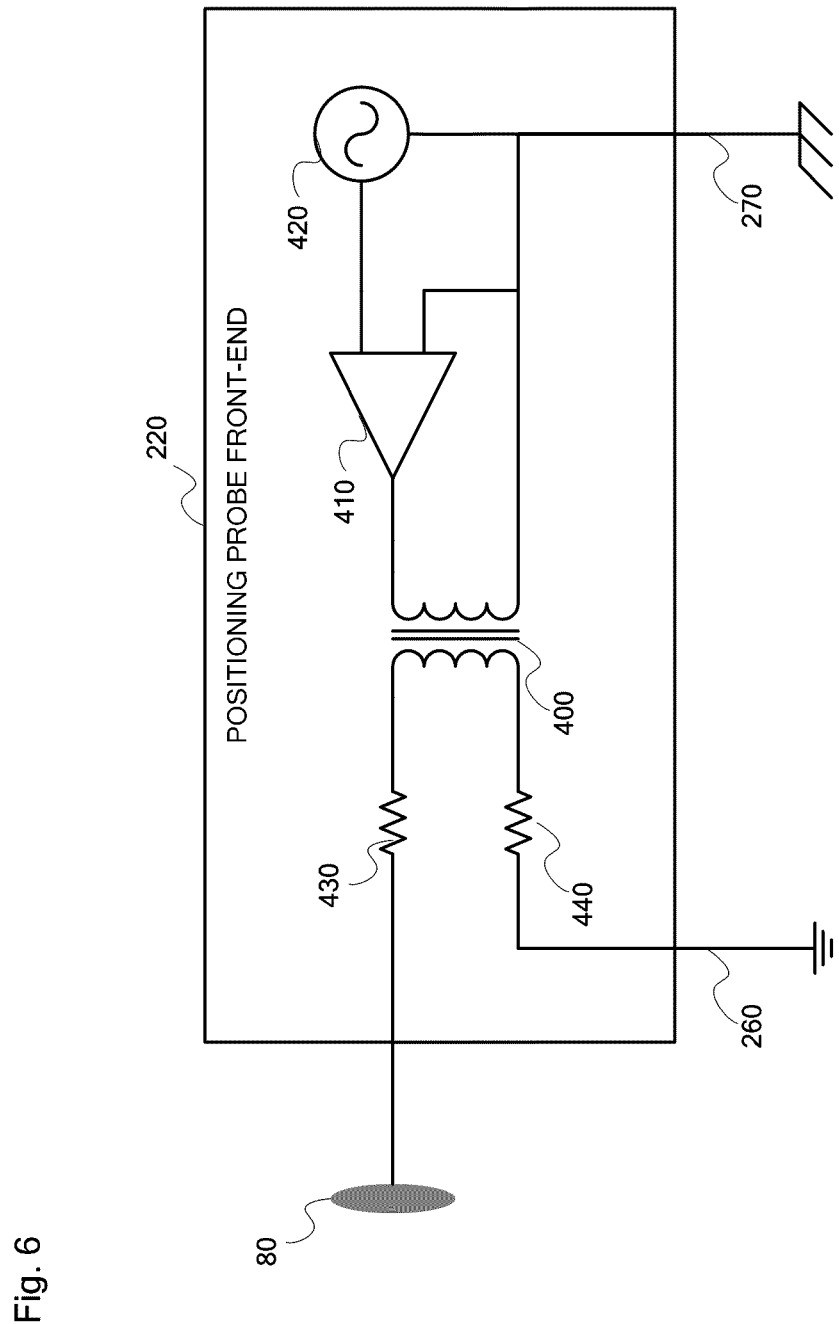
FIG. 6 is a schematic electrical diagram presenting a typical implementation of a positioning probe front-end, in accordance with an embodiment of the present invention.

FIG. 6 is a schematic electrical diagram, showing a typical implementation of positioning probe front-end 220, in accordance with an embodiment of the present invention. Front-end 220 typically comprises an isolation transformer 400, whose primary winding is fed by an operational amplifier 410 driven by an AC source 420, and whose secondary winding is coupled to positioning probe-electrode 80 and to ground 260 via resistors 430 and 440, respectively. The impedance of resistors 430 and 440 is typically much higher than that of the subject's body. For example, the impedance of resistors 430 and 440 is typically on the order of 60,000 Ohm, while the typical impedance of the human body is typically on the order of 100 Ohm. The primary winding of transformer 400 is coupled to common ground 270, while the secondary winding is coupled to positioning circuitry ground 260, which is isolated from common ground 270. Consequently, front-end 220 introduces no galvanic coupling between grounds 260 and 270. There might be some parasitic capacitance between the secondary winding of transformer 400 and ground 270, but the high value of resistor 440 reduces the effect of such parasitic capacitance, and front-end 220 maintains the isolation between grounds 260 and 270. Due to this isolation, the functional probe-electrodes do not affect the positioning currents flowing from the positioning probe-electrodes, and the accuracy of the positioning process is maintained.

Isolation transformer 400 can be further adapted to step up the voltage produced by amplifier 410 to a level suitable for driving the positioning currents, by appropriate selection of the ratio between the windings. As a typical example, transformer 400 may be adapted to step up the primary voltage by a factor of five, from 20 Volts to 100 Volts.

It will thus be appreciated that the embodiments described above are cited by way of example, and that the present invention is not limited to what has been particularly shown and described hereinabove. Rather, the scope of the present invention includes both combinations and sub-combinations of the features described hereinabove, as well as variations and modifications thereof which would occur to persons skilled in the art upon reading the foregoing description and which are not disclosed in the prior art.

What is claimed is:

1. A method for position sensing, comprising:
inserting a probe comprising a first probe-electrode and a second probe-electrode into a body of a subject;
coupling body-surface electrodes to a surface of the body;
measuring, using first circuitry coupled to at least the first probe-electrode and having a first electrical ground, currents passing between the first probe-electrode and the body-surface electrodes, the probe and the plurality of body surface electrodes defining respective paths and an impedance along each respective path;
determining position coordinates of the probe responsively to the measured currents using positioning circuitry, having a second electrical ground, coupled to at least the second probe-electrode;
isolating the first electrical ground from the second electrical ground; and
providing a predetermined inter-ground coupling impedance coupled between the first electrical ground and the second electrical ground, the inter-ground coupling impedance being higher than the impedance along each respective path; and
maintaining accuracy of the position coordinates determination by reducing parasitic capacitance between the positioning circuitry and one or more of the first electrical ground and the second electrical ground.

2. The method according to claim 1, wherein the value of the inter-ground coupling impedance is selected so as to maximize an accuracy of determining the position coordinates.

3. The method according to claim 2, wherein the inter-ground coupling impedance is between 500 and 5000 Ohm.

4. The method according to claim 1, wherein inserting the probe comprises passing the probe into a heart of the subject, and wherein coupling the second circuitry comprises measuring an electrical activity of the heart using at least the second probe-electrode.

5. The method according to claim 4, wherein both of the first and second probe-electrodes are coupled for use in both determining the position coordinates and measuring the electrical activity.

6. The method according to claim 1, wherein the first circuitry comprises a front-end comprising an isolation transformer having a primary winding and a secondary winding, which is coupled to at least the first probe-electrode, and wherein isolating the first electrical ground from the second electrical ground comprises coupling the secondary winding of the isolation transformer to the first electrical ground while the primary winding is coupled to the second electrical ground.

7. The method according to claim 1, wherein the probe has a front end, and wherein the front end of the probe measures the currents having an output impedance greater than 100,000 Ohm to transmit the currents through at least the first probe-electrode.

8. A medical system comprising:
   a probe adapted to be inserted into a body of a subject, the probe comprising a first probe-electrode and a second probe-electrode;
   a plurality of body-surface electrodes, which are adapted to be fixed to a surface of the body at respective locations, the probe and the plurality of body surface electrodes defining respective paths and an impedance along each respective path;
   first circuitry, coupled to at least the first probe-electrode and configured to measure currents passing between the first probe-electrode and the body-surface electrodes, the first circuitry having a first electrical ground;
   a positioning processor configured to determine position coordinates of the probe responsively to the measured currents;
   second circuitry, coupled to at least the second probe-electrode and having a second electrical ground, which is isolated from the first electric ground; and
   a predetermined inter-ground coupling impedance coupled between the first electrical ground and the second electrical ground, the inter-ground coupling impedance being higher than the impedance along each respective path;
   the positioning processor maintaining accuracy of the position coordinates of the probe by using the inter-ground coupling impedance for reducing parasitic capacitance between the positioning processor and one or more of the first electrical ground and the second electrical ground.

9. The system according to claim 8, wherein the value of the inter-ground coupling impedance is selected so as to maximize an accuracy of determining the position coordinates.

10. The system according to claim 9, wherein the inter-ground coupling impedance is between 500 and 5000 Ohm.

11. The system according to claim 8, wherein the probe is configured to be inserted into a heart of the subject, and wherein the second circuitry is coupled to measure an electrical activity of the heart using at least the second probe-electrode.

12. The system according to claim 11, wherein both of the first and second probe-electrodes are coupled for use in both determining the position coordinates and measuring the electrical activity.

13. The system according to claim 8, wherein the first circuitry comprises a front-end coupled to transmit the currents through at least the first probe-electrode, wherein the front-end comprises an isolation transformer having a primary winding and a secondary winding, and wherein the secondary winding of the isolation transformer is coupled to the first electrical ground while the primary winding is coupled to the second electrical ground.

14. The system according to claim 8, wherein the probe has at least one front end, and wherein the first circuitry transmits the currents through the at least one front end at least the first probe-electrode, and wherein the output impedance of the front-end is greater than 100,000 Ohm.

* * * * *